(12) United States Patent
Holguin

(10) Patent No.: US 6,653,427 B2
(45) Date of Patent: Nov. 25, 2003

(54) HYDROPHILIC POLYMERS, PRESSURE SENSITIVE ADHESIVES AND COATINGS

(75) Inventor: Daniel L. Holguin, Fullerton, CA (US)

(73) Assignee: Avery Dennison Corporation, Pasadena, CA (US)

(*) Notice: Subject to any disclaimer, the term of this patent is extended or adjusted under 35 U.S.C. 154(b) by 133 days.

(21) Appl. No.: 09/757,980

(22) Filed: Jan. 10, 2001

(65) Prior Publication Data

US 2001/0037006 A1 Nov. 1, 2001

Related U.S. Application Data

(63) Continuation-in-part of application No. 09/540,252, filed on Mar. 31, 2000, now abandoned.

(51) Int. Cl.$^7$ .............................................. C08F 220/68
(52) U.S. Cl. ..................... 526/320; 526/230; 526/317.1; 526/318.42; 526/318.4; 526/319; 526/329.2; 526/328.5; 526/325; 526/312
(58) Field of Search .......................... 526/89, 210, 212, 526/217, 317.1, 318.4, 318.42, 320, 329.2, 328.5, 930, 936, 312; 428/50

(56) References Cited

U.S. PATENT DOCUMENTS

| | | |
|---|---|---|
| 2,976,576 A | 3/1961 | Wichterle et al. |
| 3,220,960 A | 11/1965 | Wichterle et al. |
| 3,567,760 A | 3/1971 | Feldman et al. |
| 3,576,760 A | 4/1971 | Gould et al. |
| 3,813,695 A | 6/1974 | Podell, Jr. et al. |
| 3,963,685 A | 6/1976 | Abrahams |
| 4,275,138 A * | 6/1981 | Kita et al. .................. 430/157 |
| 4,303,066 A | 12/1981 | D'Andrea |
| 4,356,288 A | 10/1982 | Lewis et al. |
| 4,379,863 A | 4/1983 | Snyder |
| 4,482,577 A | 11/1984 | Goldstein et al. |
| 4,499,154 A | 2/1985 | James et al. |
| 4,563,184 A | 1/1986 | Korol |
| 4,575,476 A | 3/1986 | Podell et al. |
| 4,593,053 A | 6/1986 | Jevne et al. |
| 4,732,786 A | 3/1988 | Patterson et al. |
| 4,768,523 A | 9/1988 | Cahalan et al. |
| 4,812,549 A | 3/1989 | Muramoto et al. |
| 4,892,787 A | 1/1990 | Kruse et al. |
| 4,935,307 A | 6/1990 | Iqbal et al. |
| 4,994,267 A | 2/1991 | Sablotsky |
| 5,034,154 A | 7/1991 | Yezrielev et al. |
| 5,190,805 A | 3/1993 | Atherton et al. |
| 5,206,071 A | 4/1993 | Atherton et al. |
| 5,225,473 A | 7/1993 | Duan |
| 5,336,208 A | 8/1994 | Rosenbluth et al. |
| 5,478,631 A | 12/1995 | Kawano et al. |
| 5,508,366 A | 4/1996 | Andrist et al. |
| 5,516,865 A | 5/1996 | Urquiola |
| 5,580,565 A | 12/1996 | Tighe et al. |
| 5,665,477 A | 9/1997 | Meathrel et al. |
| 5,672,392 A | 9/1997 | De Clercq et al. |
| 5,695,484 A | 12/1997 | Cox |
| 5,700,585 A | 12/1997 | Lee |
| 5,712,346 A | 1/1998 | Lee |

FOREIGN PATENT DOCUMENTS

| | | |
|---|---|---|
| DE | 19516111 A1 | 11/1996 |
| EP | 024164 A1 | 2/1981 |
| EP | 0716929 A1 | 6/1996 |
| JP | 2-22302 A | 1/1990 |
| WO | WO 92/11825 | 7/1992 |
| WO | WO 99/06454 | 2/1999 |

OTHER PUBLICATIONS

Perera, Don. Synthesis and Rheological Properties of Soluble Poly(hydroxyethyl methacrylate) and Some Copolymers. Polymer International, vol. 36, No. 4, pp. 303–308 (Apr. 1995).

Cuang, et al. "A very Adhesive Test, AAT," Adhesive Age, vol. 40, No. 10, pp. 18–23 (1997).

E.P. Chang, "Viscoelastic Windows of Pressure–Sensitive Adhesives," J. Adhesion, vol. 34, pp. 189–200, (1991).

E. P. Chang, "Viscoelastic Properties of Pressure–Sensitive Adhesives," J. Adhesion, pp. 233–248, (1997).

* cited by examiner

Primary Examiner—Tatyana Zalukaeva
(74) Attorney, Agent, or Firm—Renner, Kenner, Greive, Bobak, Taylor & Weber

(57) ABSTRACT

A method for the preparation of gel-free poly 2-hydroxyethyl methacrylate substantially in the absence of a chain transfer agent, comprising introducing monomeric 2-hydroxyethyl methacrylate containing ethylene glycol dimethacrylate impurities in the range of about 0.05 to 0.1% by weight into a solution of alcohol and water and polymerizing. The present invention also provides a method for the preparation of gel-free homopolymer of 4-hydroxybutyl acrylate substantially in the absence of a chain transfer agent in an alcohol or in solution of alcohol and water. The present invention also provides a method for the preparation of gel-free copolymer of 2-hydroxyethyl methacrylate and 4-hydroxybutyl acrylate substantially in the absence of a chain transfer agent, comprising introducing monomeric 2-hydroxyethyl methacrylate containing ethylene glycol dimethacrylate impurities in the range of about 0.05 to 0.1% by weight with monomeric 4-hydroxybutyl acrylate into a solution of alcohol and water.

10 Claims, No Drawings

HYDROPHILIC POLYMERS, PRESSURE SENSITIVE ADHESIVES AND COATINGS

CROSS REFERENCE TO RELATED APPLICATIONS

The present invention is a continuation-in-part of U.S. Ser. No. 09/540,252, filed on Mar. 31, 2000, now abandoned.

FIELD OF THE INVENTION

This invention is related to the method of preparing hydrophilic homopolymers and copolymers and to their use as pressure sensitive adhesives, hydrogels, coatings and compositions suitable for topical application to skin.

BACKGROUND OF THE INVENTION

The family of synthetic hydrophilic polymers includes polyacrylic acid, polyvinyl pyrrolidone, polyvinyl alcohol, polyacrylamide, poly hydroxybutyl acrylate, and poly 2-hydroxyethyl methacrylate. In this family of synthetic hydrophilic polymers, poly 2-hydroxyethyl methacrylate and poly hydroxybutyl acrylate are water insoluble polymers prepared from a water soluble monomer. The other polymers require crosslinking to form a water insoluble polymer.

2-Hydroxyethyl methacrylate polymers are of interest because of their biocompatibility as evidenced by excellent performance in animal implant studies. The extensive use of 2-hydroxyethyl methacrylate polymers for contact lenses for the eyes illustrates the non irritating nature of the polymers.

Other than commercial use in contact lenses, 2-hydroxyethyl methacrylate polymers have had limited commercial success, used at low percentages only, because of the nature of the monomer. Industrial grade 2-hydroxyethyl methacrylate monomer contains a small amount of crosslinker impurity which can cause gel formation during solvent polymerization. The preparation of 2-hydroxyethyl methacrylate polymer, therefore, generally requires the use of very pure and expensive monomer or a very extensive and expensive polymerization process.

U.S. Pat. No. 2,976,576 describes the use of poly 2-hydroxyethyl methacrylate resin for contact lenses and body implants.

U.S. Pat. No. 3,220,960 describes the use of poly 2-hydroxyethyl methacrylate resin for contact lenses and body implants.

U.S. Pat. No. 3,567,760 describes the preparation of 2-hydroxyethyl methacrylate copolymers in methanol that are water soluble salts for entrapping drugs, pesticides, flavoring agents, and fragrances.

U.S. Pat. No. 3,963,685 describes the preparation of methanol soluble poly 2-hydroxyethyl methacrylate for wound care dressings using high purity 2-hydroxyethyl methacrylate monomer having not over 0.035 weight percent of alkylene glycol dimethacrylate impurities.

EP 024164A1 describes the preparation of methanol soluble poly 2-hydroxyethyl methacrylate using high purity 2-hydroxyethyl methacrylate monomer.

Polymer International, vol. 36 no. 4, pp.303–308 (April 1995), describes the preparation of dimethylformamide soluble poly 2-hydroxyethyl methacrylate using a chain transfer agent to prevent gellation.

U.S. Pat. No. 4,303,066 describes the use of a plasticized poly 2-hydroxyethyl methacrylate resin prepared from high purity monomer as a non-tacky synthetic film for skin burns, with shortened forming time by adding water to the mixture.

U.S. Pat. No. 4,593,053 describes the use of a plasticized polyvinyl pyrrolidone as a hydrophilic medical type pressure sensitive adhesive for biomedical electrodes and transdermal devices.

WO 92/11825 describes the use of plasticized poly 2-hydroxyethyl methacrylate resin as a hydrophilic medical type pressure sensitive adhesive for a medical device.

U.S. Pat. No. 5,225,473 describes the use of a UV cured plasticized polyvinyl pyrrolidone as a hydrophilic medical type pressure sensitive adhesive for biomedical electrodes and transdermal devices.

U.S. Pat. No. 5,206,071 describes acrylic graft copolymers and water soluble polymers.

EP 0716929A1 describes acrylic graft copolymers and water soluble polymers.

DE 19516111A1 describes water soluble copolymers with crosslinkers.

U.S. Pat. No. 3,813,695 discloses a rubber or latex surgical glove that is laminated with an internal plastic lining of a hydrophilic material.

U.S. Pat. No. 4,575,476 discloses a dipped rubber glove having an outer rubber layer and a lubricating layer formed of a hydrogel polymer bonded thereto to provide a skin-contacting surface of the glove.

In general, the present invention is directed to providing a cost-effective method for the preparation of hydrophilic homopolymers and copolymers with utility as films, coatings, pressure sensitive adhesives, and compositions suitable for topical application to the skin.

BRIEF SUMMARY OF THE INVENTION

A method is provided for the preparation of gel-free poly 2-hydroxyethyl methacrylate substantially in the absence of a chain transfer agent, comprising introducing monomeric 2-hydroxyethyl methacrylate containing ethylene glycol dimethacrylate impurities in the range of no more than about 0.05–0.1% by weight of the monomer, into alcohol, polymerizing the 2-hydroxyethyl methacrylate to form a polymerization mixture, and optionally removing the alcohol. The alcohol is preferably selected from one of methanol and ethanol. Hydrophilic pressure sensitive adhesives are provided by adding polyethylene glycol to the polymerization mixture prior to removing the alcohol. Flexible hydrophilic coatings also are provided by adding glycerin to the polymerization mixture prior to removing the alcohol by drying.

A method is also provided for the preparation of a gel free hydrophilic polymer substantially in the absence of a chain transfer agent comprising a copolymer of 2-hydroxyethyl methacrylate and 4-hydroxybutyl acrylate, including introducing monomeric 2-hydroxyethyl methacrylate containing no more than about 0.05–0.1% by weight of ethylene glycol dimethacrylate into an alcohol solution with 4-hydroxybutyl acrylate, polymerizing the 2-hydroxyethyl methacrylate and 4-hydroxybutyl acrylate to form a polymerization mixture, and removing the alcohol. The alcohol is selected from one of methanol and ethanol, with ethanol being preferred.

In another embodiment, the monomeric 2-hydroxyethyl methacrylate contains no more than about 3% by weight alkylene glycol methacrylate impurities, wherein the alkylene glycol methacrylate impurities are selected from the group consisting of ethylene glycol dimethacrylate, diethylene glycol monomethacrylate, methacrylic acid and mixtures thereof.

A method is also provided for the preparation of a gel free hydrophilic copolymer of 2-hydroxyethyl methacrylate and 4-hydroxybutyl acrylate substantially in the absence of a chain transfer agent comprising introducing monomeric 2-hydroxyethyl methacrylate containing no more than about 0.05–0.1% by weight of ethylene glycol dimethacrylate into a solution of water and alcohol with 4-hydroxybutyl acrylate, and polymerizing the 2-hydroxyethyl methacrylate and 4-hydroxybutyl acrylate to form a polymerization mixture.

In a preferred embodiment, the alcohol is selected from one of methanol and ethanol, with ethanol being preferred.

In another embodiment, the monomeric 2-hydroxyethyl methacrylate contains no more than about 3% by weight alkylene glycol methacrylate impurities, wherein the alkylene glycol methacrylate impurities are selected from the group consisting of ethylene glycol dimethacrylate, diethylene glycol monomethacrylate, methacrylic acid and mixtures thereof.

In another embodiment, the copolymer of 2-hydroxyethyl methacrylate and 4-hydroxybutyl acrylate is blended with a polyalkylene glycol, such as polyethylene glycol, to form a pressure sensitive adhesive.

The invention also provides a method for the preparation of a gel-free homopolymer of 4-hydroxybutyl acrylate substantially in the absence of a chain transfer agent comprising introducing monomeric 4-hydroxybutyl acrylate into alcohol, and polymerizing the 4-hydroxybutyl acrylate to form a polymerization mixture.

In another embodiment, the present invention provides a method for the preparation of a gel free hydrophilic homopolymer of 4-hydroxybutyl acrylate substantially in the absence of a chain transfer agent comprising introducing monomeric 4-hydroxybutyl acrylate into a solution of water and alcohol, and polymerizing the 4-hydroxybutyl acrylate.

In a preferred embodiment, the alcohol is selected from one of methanol and ethanol, with ethanol being preferred.

In another embodiment, the present invention provides a method for the preparation of a gel free hydrophilic homopolymer of 2-hydroxyethyl methacrylate substantially in the absence of a chain transfer agent comprising introducing monomeric 2-hydroxyethyl methacrylate containing no more than about 0.05–0.1% by weight of ethylene glycol dimethacrylate into a solution of water and alcohol, and polymerizing the 2-hydroxyethyl methacrylate.

In a preferred embodiment, the alcohol is selected from one of methanol and ethanol, with ethanol being preferred. These homopolymers of 2-hydroxyethyl methacrylate prepared are stable in solution.

In another embodiment, the monomeric 2-hydroxyethyl methacrylate contains no more than about 3% by weight alkylene glycol methacrylate impurities, wherein the alkylene glycol methacrylate impurities are selected from the group consisting of ethylene glycol dimethacrylate, diethylene glycol monomethacrylate, methacrylic acid and mixtures thereof.

DETAILED DESCRIPTION OF THE INVENTION

In one embodiment, the present invention provides a method for the preparation of a gel-free poly 2-hydroxyethyl methacrylate substantially in the absence of a chain transfer agent. The method includes introducing monomeric 2-hydroxyethyl methacrylate containing ethylene glycol dimethacrylate impurities in the range of no more than about 0.05 to 0.1% by weight into an alcohol selected from one of methanol and ethanol, polymerizing the 2-hydroxyethyl methacrylate to form a polymerization mixture, and removing the alcohol. Polymerization is induced by free radical initiation, and the alcohol is preferably removed by coating a substrate and drying the mixture. In one embodiment, the monomeric 2-hydroxyethyl methacrylate contains alkylene glycol impurities in a total amount of no more than 3% by weight, and the impurities are selected from the group consisting of ethylene glycol dimethacrylate, diethylene glycol monomethacrylate, methacrylic acid and mixtures thereof. The controlled level of impurities results in the gel free polymer, even without using ultra-pure monomer.

As described above, free radical polymerization is initiated by a suitable initiator. The initiator must be soluble in the alcohol and the 2-hydroxyethyl methacrylate monomer mixture. Suitable initiators that are soluble in alcohol include, but are not limited to, peroxides such as benzoyl peroxide, and azo compounds, such as 2,2'-azobis (isobutyronitrile).

The method of the present invention, therefore, provides for the cost effective preparation of a gel-free poly 2-hydroxyethyl methacrylate, substantially in the absence of a chain transfer agent, using industrial grade 2-hydroxyethyl methacrylate monomer. A 2-hydroxyethyl methacrylate monomer suitable for use in the method of the present invention is available from Mitsubishi Rayon, Japan.

In another embodiment, the present invention provides a method for the preparation of a gel-free poly 2-hydroxyethyl methacrylate substantially in the absence of a chain transfer agent, to achieve a hydrophilic pressure sensitive adhesive. The method includes introducing monomeric 2-hydroxyethyl methacrylate containing ethylene glycol dimethacrylate impurities in the range of about 0.05 to 0.1% by weight into an alcohol selected from one of methanol or ethanol, polymerizing the 2-hydroxyethyl methacrylate to form a polymerization mixture, adding a polyalkylene glycol, such as polyethylene glycol in a range of about 40% to about 70% by weight, based on the weight of the polymer and the polyethylene glycol, and removing the alcohol to form a hydrophilic pressure sensitive adhesive. Polymerization is induced by free radical initiation, and alcohol removal is preferably accomplished by coating the mixture onto a substrate and drying the mixture. Although the preferred polyalkylene glycol used to prepare the pressure sensitive is polyethylene glycol, other polyalkylene glycols, such as polypropylene glycol may be used. In addition, copolymers of ethylene and propylene glycol may also be used to form the pressure sensitive adhesive.

In another embodiment, the 2-hydroxyethyl methacrylate contains alkylene glycol impurities in a total amount of no more than about 3% by weight of monomer, and the impurities are selected from the group consisting of ethylene glycol dimethacrylate, diethylene glycol monomethacrylate, methacrylic acid and mixtures thereof. The hydrophilic pressure sensitive adhesives formed by this method have utility in many label and tape applications, and is particularly suitable for medical applications.

In yet another embodiment, the present invention provides a method for the preparation of a flexible hydrophilic coating comprising a gel-free poly 2-hydroxyethyl methacrylate produced substantially in the absence of a chain transfer agent. The method comprises introducing monomeric 2-hydroxyethyl methacrylate containing ethylene glycol dimethacrylate impurities in the range of about 0.05 to 0.1% by weight into an alcohol selected from one of methanol and ethanol, polymerizing the 2-hydroxyethyl methacrylate to form a polymerization mixture, adding glycerin to the polymerization mixture in an amount from about 10% to about 50% by weight of the polymer, preferably about 25% by weight of the polymer, and removing the alcohol to form a flexible hydrophilic coating. Polymerization is induced by free radical initiation, and alcohol removal by coating the mixture and drying.

In another embodiment, the 2-hydroxyethyl methacrylate contains alkylene glycol methacrylate impurities in the range of about 3%, based on the weight of the monomer. Preferably, the alkylene glycol impurities are selected from the group consisting of ethylene glycol dimethacrylate, diethylene glycol monomethacrylate, methacrylic acid and mixtures thereof, in a total amount of no more than about 3% by weight of monomer. The flexible hydrophilic coating formed by this method has utility in skin-friendly applications in which a high Moisture Vapor Transmission Rate (MVTR) is needed together with protective, skin barrier properties. The coating is also suitable for printable coatings, such as inkjet coatings for paper, plastic film, and the like.

In another embodiment, the present invention provides a method for the preparation of a gel free hydrophilic polymer substantially in the absence of a chain transfer agent comprising a copolymer of 2-hydroxyethyl methacrylate and 4-hydroxybutyl acrylate, including introducing monomeric 2-hydroxyethyl methacrylate containing 0.05 to 0.1% by weight of ethylene glycol dimethacrylate impurities, into an alcohol solution with 4-hydroxybutyl acrylate, polymerizing the 2-hydroxyethyl methacrylate and 4-hydroxybutyl acrylate to form a polymerization mixture, and removing the alcohol. The alcohol is selected from one of methanol and ethanol, with ethanol being preferred.

In another embodiment, the monomeric 2-hydroxyethyl methacrylate contains no more than about 3% by weight of alkylene glycol methacrylate impurities.

The copolymer of 2-hydroxyethyl methacrylate and 4-hydroxybutyl acrylate is a hydrophilic copolymer that is insoluble in water and does not require crosslinking for water resistance. In addition, the copolymer of 2-hydroxyethyl methacrylate and 4-hydroxybutyl acrylate is flexible enough to form a flexible coating or film for medical and skin care or skin protection applications without the need for the addition of glycerin. The flexible coating comprising the copolymer of 2-hydroxyethyl methacrylate and 4-hydroxybutyl acrylate is also useful as a Rubber or latex glove coating, with particular usefulness in wet-donning applications. rubber or latex gloves require the ability of donning, that is, the ability to slide a glove on and off the surface of the skin with minimal friction. The copolymer of 2-hydroxyethyl methacrylate and 4-hydroxybutyl acrylate provides a flexible, non-tacky glove coating that allows the donning, wet or dry, of the Rubber or latex glove with minimal blocking and without undue friction or clinging.

In another embodiment, the copolymer product of 2-hydroxyethyl methacrylate and 4-hydroxybutyl acrylate may further contain up to about 10 weight percent of an additional monomer, based on the weight of the copolymeric product. More preferably, the copolymeric product may contain from about 2 to about 4 weight percent of the additional monomer. The inclusion of up to about 10 weight percent of the monomer increases the cohesive strength of the copolymer, while still maintaining pressure sensitive adhesive properties, skin coating properties, and water resistance. Useful monomers include alkyl acrylates, alkyl methacrylates, hydroxyalkyl acrylates, hydroxyalkyl methacrylates, N-vinyl lactams, vinyl acetate and styrene monomers.

The present invention, therefore, provides a gel-free, hydrophilic copolymer of 2-hydroxyethyl methacrylate and 4-hydroxybutyl acrylate that does not to be plasticized with either water or glycerin. The copolymer of 2-hydroxyethyl methacrylate and 4-hydroxybutyl acrylate is a water-insoluble, water-absorbing, amphilic, elastic, abrasion resistant and has improved mechanical properties. Additionally, the copolymer has a high moisture vapor transmission rate that is skin friendly and, therefore, is "skin friendly."

In another embodiment, the present invention provides a copolymer of 2-hydroxyethyl methacrylate and 4-hydroxybutyl acrylate is prepared substantially in the absence of a chain transfer agent. The copolymer is prepared by introducing monomeric 2-hydroxyethyl methacrylate with 4-hydroxybutyl acrylate into a solution of water and alcohol. The monomeric 2-hydroxyethyl methacrylate should contain ethylene glycol dimethacrylate impurities in the range of about 0.05 to about 0.1% by weight. The monomers of 2-hydroxyethyl methacrylate and 4-hydroxybutyl acrylate are copolymerized to form a polymerization mixture and the alcohol/water solution is substantially removed.

The copolymerization reaction of the monomeric 2-hydroxyethyl methacrylate and 4-hydroxybutyl acrylate is carried using a water-soluble initiator system. The use of a water-soluble initiator system results in a more efficient conversion of monomers into copolymer product and, therefore, reducing the amount of residual monomer remaining after the copolymerization reaction. Reducing the amount of residual monomer remaining in the polymerization mixture avoids the need of an extensive leaching process to remove the residual monomers and the remaining water-soluble initiator, which results in a time and cost savings.

In a preferred embodiment, the monomeric 2-hydroxyethyl methacrylate contains alkylene glycol impurities in the range of no more than about 3% by weight, wherein the alkylene glycol impurities are selected from ethylene glycol dimethacrylate, diethylene glycol monomethacrylate, methacrylic acid and mixtures thereof.

In general, the copolymers of 2-hydroxyethyl methacrylate and 4-hydroxybutyl acrylate can be utilized as a topical skin coating or barrier. Some useful applications of the copolymer of 2-hydroxyethyl methacrylate and 4-hydroxybutyl acrylate includes use as sprayable carriers for topical application of drugs to the skin. For this application, the copolymer of 2-hydroxyethyl methacrylate and 4-hydroxybutyl acrylate may be mixed with an alcohol or glycol solution to produce a sprayable vehicle or carrier that can be sprayed directly onto the skin. The copolymer may also be a component of a cream, including water in oil emulsions and oil in water emulsions, lotions, which are suspensions in water or oil, ointments, which are solutions in petroleum or polyethylene glycol, or aerosols, which are sprayable solutions in water/alcohol and gels.

The copolymer of 2-hydroxyethyl methacrylate and 4-hydroxybutyl acrylate may also be a component of a transdermal drug delivery system. Specifically, the water-insoluble copolymer can be used as a carrier or vehicle to deliver an effective amount of a pharmacologically active agent (drug) transdermally. In this embodiment, the copolymer may be loaded with an effective amount of a pharmacologically active agent and locally placed on the surface of the skin. The transdermal drug delivery system can also include, as known in the art, skin permeation enhancers to facilitate the transderaml delivery of the pharmacologically active agent. The copolymer performs a dual function as a carrier of a pharmacologically active agent and a protective coating or skin barrier.

The copolymers of 2-hydroxyethyl methacrylate and 4-hydroxybutyl acrylate can be sprayed onto the skin before the application of adhesive-coated bandages, tapes, or other adhesive-coated medical devices to prevent irritation of sensitive skin.

The copolymers of 2-hydroxyethyl methacrylate and 4-hydroxybutyl acrylate can be used as an elastomeric medical film. Preferably, the copolymer of 2-hydroxyethyl methacrylate and 4-hydroxybutyl acrylate can be coated onto a substrate, such as a release liner and dried. The copolymer will be self cross-linking with heat treatment. Preferably, the copolymer will be self cross-linking by heat treating at a temperature in the range of about 70° C. to about 150° C., more preferably in a temperature range of about 70° C. to about 125° C. The elastomeric medical film can be used directly over a wound on the skin to provide a dressing or barrier. The elastomeric film is soft and pliable, and easily conforms to the contours of human skin.

The copolymers of 2-hydroxyethyl methacrylate and 4-hydroxybutyl acrylate can be used as a coating for gloves, such as rubber or latex medical gloves. The use of the copolymer of 2-hydroxyethyl methacrylate and 4-hydroxybutyl acrylate to coat a rubber or latex glove reduces the friction between the inner surface of the glove and the skin surface of the person donning the glove, especially under conditions of wet donning. The use of the copolymer of 2-hydroxyethyl methacrylate and 4-hydroxybutyl acrylate as a glove coating, therefore, alleviates the need for the use of powder or other lubricating materials with the gloves.

The copolymers of 2-hydroxyethyl methacrylate and 4-hydroxybutyl acrylate may also be included in sun block and sunscreen lotions, creams and sprays. as a carrier or vehicle of ultra-violet (UV) light absorbers, such as aminobenzoic acid, benzophenone-8 and benzophenone-4.

The copolymers of 2-hydroxyethyl methacrylate and 4-hydroxybutyl acrylate can be used as a carrier for water resistant cosmetic products. The cosmetic composition comprising the copolymer of 2-hydroxyethyl methacrylate and 4-hydroxybutyl acrylate is easy to apply to and remove from the surface of human skin, it is non-greasy, and non-occlusive. Like skin, the copolymers of 2-hydroxyethyl methacrylate and 4-hydroxybutyl acrylate are water insoluble, hydrophilic, amphilic, elastic and abrasion resistant.

The copolymer of 2-hydroxyethyl methacrylate and 4-hydroxybutyl acrylate can also be included as a component of a nasal spray or other mucus membrane drug delivery systems, as a carrier for a pharmacologically active agent, such as a pharmaceutical. Using a mucus membrane drug delivery system is a potential benefit over ingestion of pills, tablets or capsules, or repeated injections of pharmacologically active agents, because these traditional methods have initially high concentrations of the pharmacologically active agent, which may be toxic or cause side effects to the target organ or surrounding structures. As time passes, the concentration of the pharmacologically active agent diminishes and another dosage is required to maintain the pharmacologically effective level. Utilizing a mucus membrane drug delivery system including the copolymer of 2-hydroxyethyl methacrylate and 4-hydroxybutyl acrylate as a carrier for a pharmacologically active agent may permit the delivery of an effective amount of a pharmacologically active agent and maintenance of the pharmacologically effective level over longer periods of time.

In another embodiment, the copolymer of 2-hydroxyethyl methacrylate and 4-hydroxybutyl acrylate is blended with a polyalkylene glycol, such as polyethylene glycol, to form a pressure sensitive adhesive. The pressure sensitive adhesive product can be coated onto a substrate, such as a release liner. The pressure sensitive adhesive products can be used as a bandage, tape, wound dressing, surgical drapes and ostomy site dressings.

The copolymer of 2-hydroxyethyl methacrylate and 4-hydroxybutyl acrylate can further be used as a lubricant for speed swimming. The copolymer may be applied to the skin of a swimmer, for example prior to competitive swimming events. As described above, the copolymer may be applied to the skin of a swimmer by spraying the copolymer directly onto the skin.

In another embodiment, the copolymer product of 2-hydroxyethyl methacrylate and 4-hydroxybutyl acrylate, prepared in a solution of water and alcohol, may further contain up to about 10 weight percent of an additional monomer, based on the weight of the copolymeric product. More preferably, the copolymeric product may contain from about 2 to about 4 weight percent of the monomer. The inclusion of up to about 10 weight percent of the monomer increases the cohesive strength of the copolymer, while still maintaining pressure sensitive adhesive properties, skin coating properties, and water resistance. Useful monomers include alkyl acrylates, alkyl methacrylates, hydroxyalkyl acrylates, hydroxyalkyl methacrylates, N-vinyl lactams, vinyl acetate and styrene monomers.

In another embodiment, the present invention provides a method for the preparation of a gel free hydrophilic homopolymer of 4-hydroxybutyl acrylate substantially in the absence of a chain transfer agent. The method includes introducing monomeric 4-hydroxybutyl acrylate into a solution of water and alcohol, and polymerizing the 4-hydroxybutyl acrylate. As described above, the alcohol is selected from one of methanol and ethanol, with ethanol being preferred.

In another embodiment, the invention also provides a method for the preparation of a gel-free homopolymer of 4-hydroxybutyl acrylate in alcohol and substantially in the absence of a chain transfer agent comprising. The monomeric 4-hydroxybutyl acrylate is introduced into an alcohol solution. The monomeric 4-hydroxybutyl acrylate is polymerized to form a polymerization mixture.

In another embodiment, the invention provides substrates coated with the hompolymer of 4-hydroxybutyl acrylate prepared in a solution of water and alcohol and a method of coating a substrate comprising applying to the substrate the polymerization mixture of a hompolymer of 4-hydroxybutyl acrylate prepared in a solution of water and alcohol and, thereafter, removing the alcohol and water from the polymerization mixture. In a preferred embodiment, the substrate is a release liner.

In another embodiment, the invention provides a method of coating a substrate comprising applying to the substrate the polymerization mixture of a hompolymer of 4-hydroxybutyl acrylate prepared in a solution of water and alcohol, and further comprising adding a polyalkylene glycol to the polymerization mixture prior to the removing of the alcohol and water, and thereafter removing the alcohol from the polymerization mixture to form a hydrophilic pressure sensitive adhesive upon removing the alcohol and water from the polymerization mixture. The polyalkylene glycol to be added to the polymerization mixture containing the homopolymer of 4-hydroxybutyl acrylate may be selected from, but should not be limited to, polyethylene glycol, polypropylene glycol, copolymers of ethylene glycol and propylene glycol and mixtures thereof.

It should be noted, however, that the homopolymer of 4-hydroxybutyl acrylate may form a hydrophilic pressure sensitive adhesive even without the addition of a polyalkylene glycol to the polymerization mixture. However, the addition of a polyalkylene glycol to the polymerization mixture prior to removing the solution of alcohol and water may enhance the adhesive properties of the resulting pressure sensitive adhesive.

The homopolymer of 4-hydroxybutyl acrylate prepared in a solution of water and alcohol, like the copolymer of 2-hydroxylethyl methacrylate and 4-hydroxybutyl acrylate, has a wide variety of applications. As described above for the copolymer of 2-hydroxylethyl methacrylate and 4-hydroxybutyl acrylate, the homopolymer of 4-hydroxybutyl acrylate can be used to prepare elastomeric films for medical applications.

The homopolymer of 4-hydroxybutyl acrylate may also be used as a carrier for a transdermal drug delivery system or a mucus membrane drug delivery system. The carrier may be loaded with a pharmacologically active agent, such as a pharmaceutical.

The homopolymer of 4-hydroxybutyl acrylate is also useful for the preparation of creams, lotions, and ointments.

The homopolymer of 4-hydroxybutyl acrylate may also be used to prepare aerosol and spray compositions for direct application to the skin.

The homopolymer of 4-hydroxybutyl acrylate may also be used to prepare a skin friendly cosmetic composition.

The homopolymer of 4-hydroxybutyl acrylate may also be used to prepare a coating comprising the homopolymer. The coating compositions find particular application in the coating of rubber or latex gloves, such as the surgical gloves used in the medical field.

In another embodiment, the homopolymer product of 4-hydroxybutyl acrylate may further contain up to about 10 weight percent of an additional monomer, based on the weight of the polymeric product. More preferably, the polymeric product may contain from about 2 to about 4 weight percent of the monomer. The inclusion of up to about 10 weight percent of the monomer increases the cohesive strength of the homopolymer, while still maintaining pressure sensitive adhesive properties, skin coating properties, and water resistance. Useful monomers include alkyl acrylates, alkyl methacrylates, hydroxyalkyl acrylates, hydroxyalkyl methacrylates, N-vinyl lactams, vinyl acetate and styrene monomers.

In another embodiment, the present invention provides a method for the preparation of a gel free hydrophilic homopolymer of 2-hydroxyethyl methacrylate substantially in the absence of a chain transfer agent. The method includes introducing monomeric 2-hydroxyethyl methacrylate containing no more than about 0.05–0.1% by weight of ethylene glycol dimethacrylate into a solution of water and alcohol, and polymerizing the 2-hydroxyethyl methacrylate.

In a variation of this method, the monomeric 2-hydroxyethyl methacrylate contains no more than about 3% by weight alkylene glycol methacrylate impurities. Preferably, the alkylene glycol methacrylate impurities are selected from, but are not limited to, ethylene glycol dimethacrylate, diethylene glycol monomethacrylate, methacrylic acid and mixtures thereof. Again, the alcohol used in the water/alcohol mixture and into which the monomeric 2-hydroxyethyl methacrylate is introduced includes, but should not be limited to, methanol and ethanol, with ethanol being preferred.

The invention also provides a substrates coated with the homopolymer of 2-hydroxyethyl methacrylate prepared in a solution of water and an alcohol and a method of coating a substrate comprising applying to a substrate a polymerization mixture containing the homopolymer of 2-hydroxyethyl methacrylate and, thereafter, removing the alcohol and water from the polymerization mixture. In one preferred embodiment, the substrate is a release liner.

In another embodiment, the invention provides hydrophilic pressure sensitive adhesives prepared by adding a polyalkylene glycol to the homopolymer of 2-hydroxyethyl methacrylate prepared in a solution of water and alcohol, and a method of coating a substrate comprising applying to a substrate a polymerization mixture containing the homopolymer of 2-hydroxyethyl methacrylate, and further comprising adding a polyalkylene glycol to the polymerization mixture prior to the removing of the alcohol and water, to form a hydrophilic pressure sensitive adhesive upon removing said alcohol and water. In one preferred embodiment, the substrate is a release liner. The polyalkylene glycol that is added to the polymerization mixture containing the homopolymer of 2-hydroxyethyl methacrylate may be selected from, but is not limited to, polyethylene glycol, polypropylene glycol, copolymers of ethylene glycol and propylene glycol and mixtures thereof.

The homopolymer of 2-hydroxyethyl methacrylate prepared in a solution of water and alcohol, like the homopolymer of 4-hydroxybutyl acrylate, has a wide variety of applications. As described above for the homopolymers of 4-hydroxybutyl acrylate, the homopolymer of 2-hydroxylethyl methacrylate can be used to prepare elastomeric films for medical applications.

The homopolymer of 2-hydroxyethyl methacrylate may also be used as a carrier for a transdermal drug delivery system or a mucus membrane drug delivery system. The carrier may be loaded with a pharmacologically active agent, such as a pharmaceutical.

The homopolymer of 2-hydroxyethyl methacrylate is also useful for the preparation of creams, lotions, and ointments.

The homopolymer of 2-hydroxyethyl methacrylate may also be used to prepare aerosol and spray compositions for direct application to the skin.

The homopolymer of 2-hydroxyethyl methacrylate may also be used to prepare a skin friendly cosmetic composition.

The homopolymer of 2-hydroxyethyl methacrylate may also be used to prepare a coating comprising the homopolymer. The coating compositions find particular application in the coating of rubber or latex gloves, such as the surgical gloves used in the medical field.

All of the homopolymers and copolymers prepared in accordance with the methods of the present invention may also be useful as a carrier of an insect repellant for topical application to the skin.

In another embodiment, the homopolymer product of 2-hydroxyethyl methacrylate may further contain up to about 10 weight percent of an additional monomer, based on the weight of the copolymeric product. More preferably, the polymeric product may contain from about 2 to about 4 weight percent of the monomer. The inclusion of up to about 10 weight percent of the monomer increases the cohesive strength of the polymer, while still maintaining pressure sensitive adhesive properties, skin coating properties, and water resistance. Useful monomers include alkyl acrylates, alkyl methacrylates, hydroxyalkyl acrylates, hydroxyalkyl methacrylates, N-vinyl lactams, vinyl acetate and styrene monomers.

2-Hydroxyethyl methacrylate monomer suitable for use in the method of the present invention may also be made by blending industrial grade 2-hydroxyethyl methacrylate monomer from various sources to provide the desired level of impurities. Although less economical, 2-hydroxyethyl methacrylate monomer suitable for use in the method of the present invention may also be made by adding specified amounts of impurities to a higher purity 2-hydroxyethyl methacrylate monomer, to control the properties desired.

The polymers and copolymers of the present invention may be applied to various substrates as described below by any conventional means known in the art such as die coating, roll coating, reverse roll coating, gravure coating, reverse gravure coating, offset gravure coating, Mayer rod or wire wound rod coating, spraying, brushing, and the like. The polymers and copolymers of the present invention may be heated or cooled to facilitate the coating process and to alter the depth or penetration into the substrate.

The amount of the polymers and copolymers of the present invention applied to a substrate may be varied depending upon the characteristics of the substrate, the characteristics desired to be imparted to the substrate, and the particular characteristics of the polymers and copolymers. For economic reasons, it is normally desired to apply the lowest amount of coating to obtain the desired result. Typically, the applied coating weights may, depending on the substrate and intended use, range from about 0.1 to about 100 grams/meter$^2$. For pressure sensitive adhesive applications, the amount is preferably in the range of about 15 grams/meter$^2$ to about 45 grams/meter$^2$. For hydrophilic coating and ink jet coating applications, the amount is preferably from about 1 gram/meter$^2$ to about 25 grams/meter$^2$.

Composites of the present invention may be prepared in various forms including webs which may be in roll form and which can thereafter be cut or slit into strips or sheets of desired dimensions.

As described hereinabove, all of the homopolymers and copolymers prepared in accordance with the methods of the present invention have a high MVTR, are water-insoluble, are flexible, hydrophilic, are water-absorbing, and have good mechanical properties.

All of the homopolymers and copolymers prepared in accordance with the methods of the present invention are suitable for the preparation of and use as elastomeric films, pressure sensitive adhesives, coatings, hydrogels, compositions for topical applications to the skin such as, creams, lotions, ointments, gels, aerosols, sprays, cosmetic compositions, deodorants, and insect repellants.

The unique combination of characteristics makes the homopolymers and copolymer suitable as medical elastomeric films, bandages, tapes, wound care dressings, surgical drapes, ostomy site dressings, as a carrier for transdermal drug delivery systems, and as a carrier for mucus membrane drug delivery systems. Typical pharmacologically active agents include, but are not limited to, corticosteroids, anti-acne agents such as retinoic acid and benzoyl peroxide, anti-infectives such as erythromycin, tetracycline, and clindamycin, anti-fungals such as tolnaftate, undecylenic acid, nystatin, clotrimazole, and fluconazole, antioxidants such as butylated hydroxytoluene, t-butylhydroquinone, tocopherol, surfactants such as sodium lauryl sulfate, UV absorbers such as aminobenzoic acid, benzphenon-8, and benzophenone-4, humectants such as propylene glycol, glycerin, polyethylene glycol, and butylene glycol, alpha hydroxy acids, and emollients such as castor oil, mineral oil, petroleum cetyl palmitate, cetyl alcohol, and stearyl alcohol.

The homopolymers and copolymers prepared in accordance with the methods of the present invention are also useful as a protective coating for skin prior to the application of bandages, tapes or medical devices to the skin.

The following examples illustrate the methods of preparation of the hydrophilic homopolymers and copolymers of the present invention. It should be noted that the examples are intended for illustrative purposes only, and are not intended to limit the scope of the invention in any manner.

The presence of any gel in the polymeric product can be determined by pouring a thin film of the polymeric product and visually inspecting for any particulate in the thin polymeric film.

The term "gel free" as used in the specification refers to a polymeric product having no particulates on visual inspection of a poured thin film of the polymeric product. The term "% insoluble" of the homopolymers and copolymers prepared according to the methods of the present invention refers to a measure of the polymer product that is insoluble in methanol (MeOH). The % insoluble of the product may be determined as follows: The polymer product is coated onto a silicone release liner and dried at 70° C. for 15 minutes. The adhesive is removed from the release liner, and a 60 to 80 mg sample of the adhesive is accurately weighed out and placed into a 10 μm PTFE membrane filter. The edges of the filter are thermally sealed to contain the sample, and the filter is placed in a vial containing about 15 g of methanol. The vial is agitated for 72 hours, and the filter is taken out of the solvent and dried at 120° C. for 120 minutes. The filter is then weighed, and the resulting weight of the sample is used to calculate the % insoluble as follows:

$$\% \text{ insoluble}=(b/a)\times 100$$

wherein,
a=initial weight of the sample, and
b=final weight of the sample.

EXAMPLE 1

Preparation of poly 2-Hydroxyethyl Methacrylate in Ethanol Recipe (1807 Gram Batch)

| Reactor Charge | |
|---|---|
| 2-Hydroxyethyl Methacrylate (Mitsubishi) | 540 grams |
| Ethanol | 1080 grams |
| Benzoyl peroxide | 2.7 grams |
| Cook-Off initiator #1 | |
| Ethanol | 60 grams |
| 2,2'-azobis(2,4-dimethylpentanenitrile)* | 1.4 grams |
| Cook-Off initiator #2 | |
| Ethanol | 60 grams |
| 2,2'-azobis(2,4-dimethylpentanenitrile)* | 1.4 grams |

-continued

| Cook-Off initiator #3 | |
| --- | --- |
| Ethanol | 60 grams |
| 2,2'-azobis(2,4-dimethylpentanenitrile)* | 1.4 grams |

*VAZO ®52 (2,2'-azobis(2,4-dimethylpentanenitrile) (Dupont; Wilmington, Delaware)

Procedure

1. The Reactor Charge was weighed out into a flask and poured into a reaction kettle with mixing, and was heated with an 80° C. jacket and a $N_2$ purge kettle.
2. The Cook-Off initiator #1 (Ethanol and VAZO®52) was weighed into a small beaker and mixed until the solids dissolved.
3. Three and one-half hours after the addition of the Reactor Charge, Cook-Off initiator #1 was added to the kettle.
4. The Cook-Off initiator #2 (Ethanol and VAZO®52) was weighed into a small beaker and mixed until the solids dissolved.
5. One hour after the addition of Cook-Off initiator #1, Cook-Off initiator #2 was added to the kettle.
6. The Cook-Off initiator #3 (Ethanol and VAZO®52) was weighed into a small beaker and mixed until the solids dissolved.
7. One hour after the addition of Cook-Off initiator #2, Cook-Off initiator #3 was added to the kettle.
8. One hour after the addition of Cook-Off initiator #3, the kettle contents were cooled and discharged.

The polymeric product synthesized in Example No. 1, above, exhibited the following properties:

Appearance: clear to light-yellow gel-free liquid
Solids: 30.5%
Viscosity: 8,700 cPs
Residual monomer: HEMA, 0.95%
Molecular weight: 483K, PD 6.1

The appearance of the polymeric product in this example was determined utilizing a visual test looking at the clarity and color of the polymeric product. The presence of any gel in the polymeric product was determined by pouring a thin film of the product and visually inspecting for any particulate.

The percent solids in the polymeric product was measured by accurately weighing a small aluminum dish, then accurately weighing about 1 gram of wet polymer sample. The aluminum dish with the sample was dried under an infrared lamp for about 15 minutes. The aluminum dish with the dried sample was cooled and then accurately reweighed. The weight of the dried sample divided by the wet sample multiplied by 100 is the percent total solids in the sample.

The viscosity of the polymeric product was measured under ambient conditions (23–25° C.) with a Brookfield LV Viscometer using an appropriate spindle and speed for the measured viscosity. The viscosity units are centipoise, cPs.

The molecular weight of the polymeric product was measured using Gel Permeation Chromatography (GPC) in methanol with polyethylene glycol standards.

The protocols described hereinabove that were used to measure and evaluate the appearance, percent solids, viscosity and molecular weight of the polymeric product of Example No. 1 apply to all of the representative homopolymer and copolymer products produced according to the present invention, unless specifically indicated.

Example Nos. 2–6 are representative poly 2-hydroxyethyl methacrylates prepared in ethanol according to the present invention with 2-hydroxyethyl methacrylate monomers having alkylene glycol methacrylate impurities less than 3%, and wherein the alkylene glycol methacrylate impurities comprise ethylene glycol dimethacrylate impurities are between 0.05 and 0.1% by weight, and are compared to Comparative Example Nos. 7 and 8, which are poly 2-hydroxyethyl methacrylates prepared with 2-hydroxyethyl methacrylate monomers having alkylene glycol methacrylate impurities less than 3% and with ethylene glycol dimethacrylate greater than 0.15%. As Table I shows, substantially gel-free hydrophilic poly 2-hydroxyethyl methacrylates can be synthesized in ethanol. The poly 2-hydroxyethyl methacrylates can achieve molecular weights, Mw (weight average molecular weight), from about 176,000 to about 1,000,000, molecular weights, Mn (number average molecular weight), from about 59,000 to about 250,000, solids contents of about 30 weight percent, and a viscosity of about 1000 to about 100,000 cPs.

TABLE I

Synthesis of Poly 2-hydroxyethyl methacrylate in Ethanol

| Example No. | 2 | 3 | 4 | 5 | 6 | C7 | C8 |
| --- | --- | --- | --- | --- | --- | --- | --- |
| HEMA used[a] | Mitsubishi | Mitsubishi | Mitsubishi | Mitsubishi | Mitsubishi | Rohm & Haas | Rohm & Haas |
| Initiator | AIBN[b], 0.5% | BPo[c], 0.5% | BPo, 0.5% | BPo, 0.5% | BPo, 0.25% | AIBN, 0.5% | AIBN, 0 5% |
| Solids Content, % | 30 | 30.9 | 30.5 | 30.7 | 31.3 | gelled | gelled |
| Viscosity, cPs | 1090 | 7100 | 8700 | 15150 | 82,000 | — | — |
| Mol. wt, Mw | 176,000 | 420,000 | 483,000 | 874,000 | 1,070,000 | — | — |
| Mol. wt, Mn | 59,200 | 68,000 | 78,700 | 187,000 | 252,000 | — | — |

[a]source of 2-hydroxyethyl methacrylate monomer
[b]AIBN (azobisisobutyronitrile)
[c]BPo(Benzoyl Peroxide)

Table I shows that the preparation of poly 2-hydroxyethyl methacrylate (poly HEMA) polymers, substantially in the absence of chain transfer agents, using the Mitsubishi HEMA monomer source having acceptable impurity levels provides high molecular weight gel free poly HEMA solution in alcohol. The molecular weight of the polymers can be varied by adjusting the type and amount of initiator used. The use of the AIBN initiator provides the lowest molecular weight polymer. In contrast, the poly HEMA prepared with Rohm & Haas HEMA monomer having 0.17% ethylene glycol dimethacrylate impurity levels, provided a gelled poly HEMA in alcohol, even when using AIBN as the initiator.

EXAMPLE 9

Preparation of poly 2-Hydroxyethyl Methacrylate in Methanol Recipe (982 Gram Batch)

| Reactor Charge | |
| --- | --- |
| 2-Hydroxyethyl Methacrylate (Mitsubishi) | 300 grams |
| Methanol | 700 grams |
| AIBN (2,2'-azobis(isobutyronitrile) | 1.5 grams |
| Cook-Off initiator | |
| Methanol | 15 grams |
| AIBN (2,2'-azobis(isobutyronitrile) | 0.75 grams |

Procedure

1. The Reactor Charge was weighed out into a flask and poured into a reaction kettle with mixing, and was heated with an 65° C. jacket and a $N_2$ purge kettle.
2. The Cook-Off initiator (Methanol and AIBN) was weighed into a small beaker and mixed until the solids dissolved.
3. Six hours after adding the Reactor Charge the Cook-Off initiator was added.
4. Four hours after adding the Cook Off initiator, the kettle contents were cooled and discharged.

The polymeric product synthesized in Example No. 9, above, exhibited the following properties:

Appearance: clear to light-yellow gel-free liquid

Solids: 36.7%

Viscosity: 39,000 cPs

Residual monomer: HEMA, 0.78%

Molecular weight: Mw=2,260K, PD 4

The shear (min) and 180° peel adhesion properties of pressure sensitive adhesives prepared according to the present invention was evaluated. Table II, below, shows the shear properties and peel adhesion properties of pressure sensitive adhesives on substrates, such as stainless steel, high density polyethylene, and recycled cardboard. As Table II shows, pressure sensitive adhesives prepared by blending poly 2-hydroxyethyl methacrylate synthesized in methanol with 2-hydroxyethyl methacrylate monomers having alkylene glycol methacrylate impurities less than 3% by weight and with ethylene glycol dimethacrylate less than 0.1% and polyethylene glycol (PEG) have a 180° peel adhesion after twenty minutes of about 0.75 lb/in to about 4 lb/in on a stainless steel substrate, a 180° peel adhesion of about 0.2 lb/in to about 0.4 lb/in on a high density polyethylene substrate, and a 180° peel adhesion of about 1 lb/in to about 2 lb/in on a recycled cardboard substrate.

Table II also shows that pressure sensitive adhesives prepared by blending poly 2-hydroxyethyl methacrylate prepared with 2-hydroxyethyl methacrylate monomers having alkylene glycol methacrylate impurities less than 3% by weight and with ethylene glycol dimethacrylate impurity less than 0.1% with polyethylene glycol has a 180° peel adhesion after 24 hours of about 2.3 lb/in to about 4.3 lb/in on a stainless steel substrate, a 180° peel adhesion of about 0.3 lb/in to about 1 lb/in on a high density polyethylene substrate, and a 1800 peel adhesion of about 2 lb/in to about 3.7 lb/in on a recycled cardboard substrate.

TABLE II

Poly 2-Hydroxyethyl Methacrylate synthesized in Methanol and Pressure Sensitive Adhesives

| Example No. | Resin/PEG | Coat Weight g/m² | Shear, min ¼ in², 500 g | 180° Peel, lb/in 20', SS | 180° Peel, lb/in 20', HDPE | 180° Peel, lb/in 20' RC | 180° Peel, lb/in 24 h, SS | 180° Peel, lb/in 24 h, HDPE | 180° Peel, lb/in 24 h RC |
| --- | --- | --- | --- | --- | --- | --- | --- | --- | --- |
| 10 | 1:1 | 38.1 | 2 c | 0.75 p | 0.2 p | 2.0 sl. c | 2.3 p | 0.3 p | 3.6 c |
| 11 | 1.2:0.8 | 33.6 | 98 c | 4.0 pt | 0.4 p | 1.7 sl. pt | 4.2 pt | 1.0 p | 3.7 pt |
| 12 | 1.3:0.7 | 30.7 | 143 c | 3.5 pt | 0.3 p | 1.1 sl. pt | 4.3 pt | 0.6 p | 2 0 pt |

SS - stainless steel;
HDPE - high density polyethylene;
RC - recycled cardboard
c - cohesive;
p - panel;
pt - paper tear;
sl. - slight Table II shows that polyHEMA polymers prepared in alcohol can be formulated with a plasticizer, such as polyethylene glycol (PEG) 400 (Carbowax; Union Carbide) to provide a pressure sensitive adhesive. The adhesive performance of the pressure sensitive adhesive can be varied by adjusting the amount of polyethylene glycol used in the preparation. A polyHEMA:PEG ratio in the range of about 1.5:0.5 to about 0.5:1.5 is used to prepare the pressure sensitive adhesive. Preferably, a polyHEMA:PEG ratio of about 1.2:0.8 is used to prepare the pressure sensitive adhesive.

Static shear measures the time required to remove a test sample from a substrate under a specific load. The test applies to the static force to remove an affixed pressure sensitive adhesive from a standard flat surface when the load acts parallel to the surface in a pure shearing action. In static shear testing, the samples were cut into 12×51 mm test strips. The test strips were applied to brightly annealed, highly polished stainless steel test panels having a typical size of about 50×75 mm, making a sample overlay of 12×12 mm with the test panel. The sample portion on the test panel was rolled on using a 2 kg, 5.45 pli 65 shore "A" rubber-faced roller, rolling back and forth one at a rate of 30 cm/min. After a dwell time of at least 15 minutes under standard laboratory testing conditions, the test panels with the test strips were placed at a 2° angle from the vertical, and a load of 500 g was attached to the end of the test strips. The time (in minutes) for the test sample to fail cohesively was measured by a timer.

To measure the peel adhesion, the adhesive was coated at an approximate coat weight of 25 g/m² (1.0 mil) onto a silicone coated release liner, and then laminated to a 2 mil Mylar™ facestock to form a laminate construction. The resulting laminate was die-cut into 25×204 mm sized test strips. The test strips were then applied to 50×152 mm brightly annealed, highly polishes stainless steel test panels in the lengthwise direction, and rolled down using a 2 kg 5.45 pli 65 shore "A" rubber faced roller. The roller was rolled back and forth once over the test strip at a rate of 30 cm/min. The samples were conditioned for either 15 minutes or 24 hours in a controlled environment testing room maintained at 20° C. and 50% relative humidity. After conditioning, the test strips were peeled away from the test panel in an Instron Universal Tester according to a modified version of the standard tape method Pressure-Sensitive Tape Council, PSTC-1. The force to remove the adhesive test strips from the test panel was measured in lbs/in. Glass panels and high density polyethylene panels were also used to measure peel adhesion.

Possible adhesion failure modes were: "panel failure," wherein the adhesive construction detached from the panel cleanly, without leaving any residue; "panel staining," wherein the adhesive construction detached cleanly, but left a faint stain or "shadow" on the panel; "cohesive failure," wherein the adhesive construction split apart, leaving residue on the test panel and the facestock; "facestock failure," wherein the adhesive completely detached from the facestock, and transferred to the test panel; and "mixed," wherein mixed failure modes were evident.

EXAMPLE 13

Preparation of HEMA/4-HBA Copolymer in Alcohol Recipe (1003.75 g Batch)

| Reactor Charge | |
| --- | --- |
| 2-Hydroxyethyl Methacrylate (Mitsubishi) | 150 g |
| 4-Hydroxybutyl Acrylate (4-HBA) | 150 g |
| Ethanol | 600 g |
| Benzoyl Peroxide | 1.5 g |
| Cook-Off Initiator #1 | |
| Ethanol | 33.3 g |
| AIBN (2,2'-azobis[isobutyronitrile]) | 0.75 g |
| Cook-Off Initiator #2 | |
| Ethanol | 33.3 g |
| AIBN (2,2'-azobis[isobutyronitrile]) | 0.75 g |
| Cook-Off Initiator #3 | |
| Ethanol | 33.3 g |
| AIBN (2,2'-azobis[isobutyronitrile]) | 0.75 g |

Procedure

1. The Reactor Charge was weighed out into a flask and poured into a reaction kettle with mixing, heated with a 80° C. jacket, and $N_2$ purged.
2. The Cook-Off Initiator #1 (Ethanol and AIBN) was weighed into a small beaker and mixed until the solids dissolved.
3. Three and one-half hours after adding the Reactor Charge, the Cook-Off Initiator #1 was poured into the reaction kettle.
4. Cook-Off Initiator #2 (Ethanol and AIBN) was weighed into a small beaker and mixed until the solids dissolved.
5. One hour after adding Cook-Off #1, Cook-Off #2 was added.
6. Cook-Off Initiator #3 (Ethanol and AIBN) was weighed into a small beaker and mixed until the solids dissolved.
7. One hour after adding Cook-Off #2, Cook-Off #3 was added.
8. One hour after adding Cook-Off #3, the kettle contents were cooled, then discharged into a quart jar.

The copolymer product synthesized in Example No. 14, above, exhibited the following properties:

Appearance: clear, light yellow gel-free liquid.

Solids: 30.5%

Viscosity: 844 cPs

Residual monomer: HEMA<0.01%, 4-HBA 0.22%

Glass Transition Temperature, $T_g$, 5° C.

% Gel in water: 98%

The copolymer is swellable in water up to twice its weight.

Examples 14–21 are copolymers of 2-hydroxyethyl methacrylate and 4-hydroxybutyl acrylate having varying ratios of 2-hydroxyethyl methacrylate to 4-hydroxybutyl acrylate, and which were prepared substantially in accordance with the procedure of Example 13. The moisture vapor transmission rate (MVTR) and mechanical properties, including % strain at peak, stress at peak, stress at 2% elongation, and Young's modulus, of the copolymers of 2-hydroxyethyl methacrylate and 4-hydroxybutyl acrylate were tested. The results of the evaluation of the moisture vapor transmission rate and mechanical properties are shown in Table IIIa.

Moisture Vapor Transmission Rate (MVTR) is a measure to describe the ability of a film to allow moisture vapor to pass through over specific period of time and under a controlled temperature and atmospheric pressure. With particular reference to skin applications, such as protective films and coatings, the MVTR is a measure of a film's ability to move vapor away from the skin of a patient. The MVTR was measured according to INDA Standard IST 70.4 (99). The samples were coated on a 1 mil thick MVTR film commercially available from Mylan Technologies (St. Albans, Vt.; U.S.A.) under the designation Medifilm 390 at a coat weight of 25 to 35 g/m².

TABLE IIIa

| | | | Tensile Testing | | | | |
|---|---|---|---|---|---|---|---|
| Example | Ratio HEMA/ 4HBA | $T_g$ | % Strain at peak | Stress at peak (psi) | Stress at 2% yield (psi) | Young's Modulus (psi) | MVTR g/m²/day |
| 14 | 50/50 | 5° C. | too soft | — | — | — | 3440 |
| 15 | 60/40 | 20° C. | 266 | 1035 | 216 | 5,585 | 2880 |
| 16 | 67/33 | 26° C. | 166 | 1618 | 910 | 38,211 | 2590 |
| 17 | 70/30 | 29° C. | 6.7 | 2142 | 1583 | 59,657 | 1980 |
| 18 | 75/25 | 36° C. | 4.9 | 4026 | 2520 | 145,714 | 1920 |
| 19 | 80/20 | 54° C. | too brittle | — | — | — | 2650 |
| 20 | 100/0 | 70° C. | too brittle | — | — | — | 2156 |
| 21 | 0/100 | −30° C. | — | — | — | — | 4330 |

Coatings of the copolymers of 2-hydroxyethyl methacrylate and 4-hydroxybutyl acrylate were also evaluated for abrasion resistance of the coating to cloth to simulate the abrasion resistance of the copolymer to clothing.

The abrasion resistance of the copolymers of 2-hydroxyethyl methacrylate and 4-hydroxybutyl acrylate of Examples 14–20, prepared in accordance with the methods of the present invention, were evaluated for abrasion resistance by a modified Southerland Rub Test (ASTM D1331-89). The results of the abrasion resistance studies are set forth in Table IIIb.

TABLE IIIb

| | Ratio HEMA/ | Southerland Rub Test 4 lbs, 200 strokes | |
|---|---|---|---|
| Example | 4HBA | Coating against coating | Coating against cloth |
| 14 | 50/50 | failed, too tacky | slight abrasion |
| 15 | 60/40 | few scratches | slight abrasion |
| 16 | 67/33 | scratches & abrasion | slight abrasion |
| 17 | 70/30 | scratches & abrasion | no abrasion |
| 18 | 75/25 | scratches & abrasion | slight abrasion |
| 19 | 80/20 | scratches & abrasion | slight abrasion |
| 20 | 100/0 | scratches & abrasion | slight abrasion |

As shown in Table IIIb, above, coatings comprising a copolymer of 2-hydroxyethyl methacrylate and 4-hydroxybutyl acrylate, prepared in accordance with the methods of the present invention, exhibit only slight abrasion when rubbed against cloth and, therefore, appear useful as skin coatings or barriers.

The surface tension of copolymers of 2-hydroxyethyl methacrylate and 4-hydroxybutyl acrylate and copolymers of 2-hydroxyethyl methacrylate and 4-hydroxybutyl acrylate containing 0.1%, 0.2%, 0.5% or 1% of a silicone surfactant were determined and compared to the surface tensions of water and ethanol. The results of the surface tension testing is set forth in Table IIIc.

TABLE IIIc

| | Surface Tension | |
|---|---|---|
| Example No. | | Surface Tension dynes/cm |
| 22 | water | 74.1 |
| 23 | ethanol | 24.1 |
| 24 | copolymer of 2-HEMA/4-HBA | 30.4 |
| 25a | copolymer of 2-HEMA/4-HBA 0.1% surfactant | 26 |

TABLE IIIc-continued

| | Surface Tension | |
|---|---|---|
| Example No. | | Surface Tension dynes/cm |
| 25b | copolymer of 2-HEMA/4-HBA 0.2% surfactant | 24.1 |
| 25c | copolymer of 2-HEMA/4-HBA 0.5% surfactant | 23.9 |
| 25d | copolymer of 2-HEMA/4-HBA 1% surfactant | 23.3 |

As shown in Table IIIc, above, the copolymer of 2-hydroxyethyl methacrylate and 4-hydrobutyl acrylate has a surface tension of about 30 dynes/cm. The addition, of at least 0.1% of a silicon surfactant to the copolymer of 2-hydroxyethyl methacrylate and 4-hydrobutyl acrylate reduces the surface tension of the copolymer to 26 dynes/cm or lower.

In general, to "wet" a surface, it is necessary to use a material that has a surface tension that is similar to and, preferably, lower than the surface tension of the surface to be "wetted." Human skin has a surface tension of about 27 dynes/cm. To "wet" the surface of human skin, it is necessary to utilize a material that possesses a surface tension that is similar than the surface tension of human skin. Using a copolymer 2-hydroxyethyl methacrylate and 4-hydrobutyl acrylate, it is possible to provide a continuous copolymer coatings for the surface of human skin without experiencing bleeding or gaps therein.

EXAMPLE 26

Preparation of Copolymer of 2-hydroxyethyl Methacrylate and 4-hydroxybutyl Acrylate in an Ethanol/Water Solution Recipe (1002.4 Gram Batch)

| Reactor Charge | |
|---|---|
| 2-Hydroxyethyl Methacrylate (Mitsubishi) | 200 grams |
| 4-Hydroxybutyl acrylate | 100 grams |
| Ethanol | 400 grams |
| Deionized Water | 260 grams |

-continued

| Initiator Charge | |
|---|---|
| Deionized Water | 10 grams |
| Sodium Persulfate (0.5%) | 1.5 grams |
| Cook-Off Initiator #1 | |
| Deionized Water | 10 grams |
| Sodium Persulfate | 0.3 grams | poly-2-hydroxyethyl methacrylate prepared in an alcohol/water mixture, or a copolymer of poly-2-hydroxyethyl methacrylate and poly-4-hydoxybutyl acrylate prepared in an alcohol/water mixture as described above.

Each of the pressure sensitive adhesive compositions were evaluated for static shear properties and peel adhesion properties on stainless steel substrates and polymeric substrates, such as high density polyethylene (HDPE). The results of the tests are shown in Table IVa.

TABLE IVa

| Ex. | HEMA/ 4-HBA | Polymer/ PEG | Shear, min. ¼ in². 500 g | 180° Peel, lb/in 15 min., SS | 180° Peel, lb/in 15 min., HDPE | 180° Peel, lb/in 24 hr., SS | 180° Peel, lb/in 24 hr, HDPE |
|---|---|---|---|---|---|---|---|
| 27 | 0/100 | 100/0 | 4,260 (+) | 3.423 (ft) | 0.695 (cl) | 4,187 (ft) | 2.165 (cl) |
| 28 | 50/50 | 75/25 | 63.4 (sp) | 3.391 (cl) | 1.116 (cl) | 3.761 (cl) | 0.937 (cl) |
| 29 | 100/0 | 60/40 | 223.4 (sp) | 2.973 (cl) | 0.466 (cl) | 3.042 (ft) | 0.865 (cl) |

-continued

| Cook off Initiator #2 | |
|---|---|
| Deionized Water | 10 grams |
| Sodium Persulfate | 0.3 grams |
| Cook off Initiator #3 | |
| Deionized Water | 10 grams |
| Sodium Metabisulfite | 0.3 grams |
| Total | 1002.4 grams |

Procedure

1. The Reactor Charge was weighed out into a flask and poured into a reaction kettle with mixing, and was heated with an 80° C. jacket and a N2purge kettle.
2. The Cook-Off initiator #1 was weighed into a small beaker and mixed until the solids dissolved.
3. About three hours after the addition of the Reactor Charge, Cook-Off initiator #1 was added to the kettle.
4. The Cook-Off initiator #2 was weighed into a small beaker and mixed until the solids dissolved.
5. About one hour after the addition of Cook-Off initiator #1, Cook-Off initiator #2 was added to the kettle.
6. The Cook-Off initiator #3 was weighed into a small beaker and mixed until the solids dissolved.
7. One hour after the addition of Cook-Off initiator #2, Cook-Off initiator #3 was added to the kettle.
8. About one-half hour after the addition of Cook-Off initiator #3, the kettle contents were cooled and discharged.

The polymeric product synthesized in Example No. 14, above, exhibited the following properties:

| Appearance: | clear to light-yellow gel-free liquid |
|---|---|
| Solids: | 30% |
| Residual monomers | |
| 2-Hydroxyethyl Methacrylate | 0.02% |
| 4-Hydroxtbutyl Acrylate | <0.01% |

Pressure sensitive adhesives were prepared comprising either the homopolymer of poly-4-hydoxybutyl acrylate prepared in an alcohol/water mixture, a homopolymer of The tack of the pressure sensitive adhesive was determined by a modified spherical probe adhesion test that involves recording and analyzing the entire stress-strain behavior of a pressure sensitive adhesive during bonding and debonding of the probe. The test apparatus consists of a stainless steel spherical probe connected to a force transducer. The force transducer measures the force acting upon the spherical probe. The probe is moved up and down by a rotating screw driven by a stepping motor. A pressure sensitive adhesive sample is bonded adhesive side up to the test platform with a double-sided tape. During bonding of the probe to the pressure sensitive adhesive, the probe moves down and compresses the adhesive to a pre-determined force (i.e.—compression force). During the debonding process, the probe ascends and separates from the pressure sensitive adhesive sample and a pre-determined test speed. As the probe ascends, the adhesive sample becomes elongated and exerts a tensile force on the transducer. As the adhesive is further elongated, the stress increases in the adhesive until it reaches the interfacial strength between the probe and the adhesive, at which point the probe separates from the adhesive sample. The debonding strength of the adhesive sample is measured by the magnitude of the force and duration time of the probe. The results of the tests are shown in Table VIb, below. For a detailed description for the measurement of the tack of pressure sensitive adhesives, see "Avery Adhesive Test, AAT", *Adhesives Age*, Vol. 10, No. 10, pp.18–23 (1997).

TABLE IVb

| Ex. | HEMA/ 4-HBA Copolymer | Polymer/PEG | Force (N) | Energy Nm x 10⁻⁵ |
|---|---|---|---|---|
| 27 | 0/100 | 100/0 | 0.977 | 0.144 |
| 28 | 50/50 | 75/25 | 1.359 | 0.079 |
| 29 | 100/0 | 60/40 | 1.089 | 0.024 |

As described hereinabove, the copolymers of 2-hydroxyethyl methacrylate and 4-hydrobutyl acrylate prepared according to the method of the present invention possess the capability to undergo self crosslinking with thermal treatment. Examples 30–33 are copolymers of 2-hydroxyethyl methacrylate and 4-hydroxybutyl acrylate prepared in ethanol, where the ratio of HEMA to 4-HBA is 67/33. Examples 34–37 are copolymers of 2-hydroxyethyl methacrylate and 4-hydroxybutyl acrylate prepared in a solution of ethanol and water, where the ratio of HEMA to 4-HBA is 60/40. Examples 38–41 are copolymers of 2-hydroxyethyl methacrylate and 4-hydroxybutyl acrylate prepared in a solution of ethanol and water, where the ratio of HEMA to 4-HBA is 50/50. All of the copolymer products were cast into films and the films were dried at 70° C. for 15 minutes. Thereafter, the percent (%) insoluble, percent (%) strain at break, and Young's modulus were tested for each copolymer product. Comparative Examples 30, 34, and 38 were dried at 70° C. for 15 minutes, but were not cured further.

The strain of a particular body refers to the change in the dimensions of that body in response to an applied force. The Young's modulus of a particular body refers to the ratio between the compressive stress and the elongation of a solid body. The % strain at break and the Young's modulus of the copolymers of 2-hydroxyethyl methacrylate and 4-hydroxybutyl acrylate were determined according to ASTM Standard D 638M (93) using dumbell-shaped test samples.

The results of the tensile testing and percent insoluble in methanol of samples are reported in Table V below.

TABLE V

|  |  |  | Tensile Testing | | |
| --- | --- | --- | --- | --- | --- |
| Ex. | HEMA/ 4-HBA ratio | Curing condiditons | % Strain at break | Young's Modulus, psi | % insoluble in MeOH |
| C30 | 67/33 | — | 253.5 | 17227 | 33.8 |
| 31 | 67/33 | 100° C., 5 min | 195.3 | 23489 | 56.8 |
| 32 | 67/33 | 125° C., 5 min | 184.2 | 31192 | 67.1 |
| 33 | 67/33 | 150° C., 5 min | 150 | 59470 | 89.7 |
| C34 | 60/40 | — | 399.4 | 500.2 | 59.3 |
| 35 | 60/40 | 100° C., 5 min | 383.4 | 1499.6 | 60.6 |
| 36 | 60/40 | 125° C., 5 min | 342.7 | 3917.4 | 59.1 |
| 37 | 60/40 | 150° C., 5 min | 328.8 | 5514.1 | 75.3 |
| C38 | 50/50 | — | 564.9 | 89 | 53.1 |
| 39 | 50/50 | 100° C., 5 min | 524.9 | 193.5 | 61.6 |
| 40 | 50/50 | 125° C., 5 min | 495.3 | 148.6 | 72 |
| 41 | 50/50 | 150° C., 5 min | 356.8 | 449.3 | 83 |

As shown in Table V, the copolymers of HEMA and 4-HBA can be self-crosslinked with thermal treatment only. The cured copolymers exhibit lower strains at break and higher moduli as compared to the uncured copolymers. The ability to self crosslink is especially beneficial where the copolymeric product is intended to be utilized for skin applications and, therefore, it would be advantageous to avoid the use crosslinking agents that may be toxic.

EXAMPLE 42

Preparation of Copolymer of 2-hydroxyethyl Methacrylate and 4-hydroxybutyl Acrylate in an Ethanol/Water Solution Recipe

| Reactor Charge | |
| --- | --- |
| 2-Hydroxyethyl Methacrylate (Mitsubishi) | 16.64 Kg |
| 4-Hydroxybutyl acrylate | 8.32 Kg |

| -continued | |
| --- | --- |
| Ethanol | 24.12 Kg |
| Deionized Water | 24.12 Kg |
| Initiator Charge | |
| Deionized Water | 0.41 Kg |
| Sodium Persulfate | 0.13 Kg |
| Cook-Off Initiator #1 | |
| Deionized Water | 0.2 Kg |
| Ethanol | 0.2 Kg |
| Sodium Persulfate | 0.025 Kg |
| Cook off Initiator #2 | |
| Deionized Water | 0.2 Kg |
| Ethanol | 0.2 Kg |
| Sodium Persulfate | 0.025 Kg |
| Cook off Initiator #3 | |
| Deionized Water | 0.2 Kg |
| Ethanol | 0.2 Kg |
| Sodium Metabisulfite | 0.025 Kg |
| Total | 75.4 Kg |

Procedure

1. Begin heating reactor with a 83° C. jacket and with a $N_2$ purge.
2. The Reactor Charge was weighed out into a weight tank and transferred to the reactor with mixing.
3. When Reactor Charge reaches a temperature of about 76° C., the Initiator Charge was added to the reactor.
4. With reaction temperature going to 85° C. Start hold period. Hold for three hours (reaction to 77.5° C.).
5. The Cook-Off initiator #1 was weighed into a beaker, and mixed until the solids dissolved.
6. About three hours after the addition of the Reactor Charge, Cook-Off initiator #1 was added to the reactor.
7. The Cook-Off initiator #2 was weighed into a beaker and mixed until the solids dissolved.
8. About one hour after the addition of Cook-Off initiator #1, Cook-Off initiator #2 was added to the reactor.
9. The Cook-Off initiator #3 was weighed into a beaker and mixed until the solids dissolved.
10. On e hour after the addition of Cook-Off initiator #2, Cook-Off initiator #3 was added to the reactor.
11. About one hour after the addition of Cook-Off initiator #3, the reactor contents were cooled and the leaching process started.

Samples of the polymerization product were taken from the reactor every hour throughout the reaction to evaluate the conversion of the monomers to the copolymeric product and the residual monomers remaining in the reactor. The amount of the residual monomers remaining in the reactor after each hour of the reaction are shown in Table VI below.

TABLE VI

|  | Residual Monomer | |
| --- | --- | --- |
| Hour | HEMA | 4-HBA |
| 1 | 0.25% | 0.45% |
| 2 | 82 ppm | 700 ppm |
| 3 | 85 ppm | 360 ppm |
| 4 | 90 ppm | 120 ppm |
| 5 | 80 ppm | 50 ppm |
| 6 | 50 ppm | <10 ppm |

As is shown in Table VI, one hour after the addition of Cook-Off Initiator #3, the reaction mixture only contains 55 ppm HEMA residual monomer and <10 ppm 4-HBA residual monomer. These results demonstrate that the copolymerization of HEMA and 4-HBA in a solution of alcohol and water results in a very efficient conversion of monomer into copolymer product with a very low occurrence of residual monomer in the final copolymeric product.

It should be noted that a leaching process may also be utilized to remove any residual monomers and initiators, thus further purifying the copolymeric product of HEMA and 4-HBA. A suitable leaching process for use with the polymer prepared according the present invention is set forth below.

Leaching Process

| First Leach | |
|---|---|
| Water to precipitate polymer | 94.1 Kg |
| Decant off effluent | 93.3 Kg |
| Ethanol to redissolve | 7.5 Kg |
| Residual monomer remaining after first leach: | |
| HEMA | <50 ppm |
| 4-HBA | <10 ppm |
| Second Leach | |
| Water to precipitate polymer | 74.8 Kg |
| Decant off effluent | 92.9 Kg |
| Ethanol to redissolve | 7.5 Kg |
| Residual monomer remaining after second leach: | |
| HEMA | <50 ppm |
| 4-HBA | <10 ppm |
| Third Leach | |
| Water to precipitate polymer | 74.8 Kg |
| Decant off effluent | 81.5 Kg |
| Ethanol to redissolve | 9.4 Kg |
| Residual monomer remaining after first leach: | |
| HEMA | <50 ppm |
| 4-HBA | <10 ppm |

The leached polymeric product synthesized in Example No. 42, above, exhibited the following properties:

| | |
|---|---|
| Viscosity, cPs | 660 |
| % Solids content | 23.6% |
| % Ethanol | 23.5% |
| % Water | 52.9% |
| Residual monomers | |
| 2-Hydroxyethyl Methacrylate | <50 ppm |
| 4-Hydroxybutyl Acrylate | <10 ppm |

Extensive leaching processes have been conventionally used in the art to remove residual monomers, initiators, and other reactants from the final polymeric products require the use of elevated temperatures, reduced pressures, centrifugation and/or multiple washes. To the contrary, all of the polymeric products prepared by the methods of the present invention have very low levels of residual monomers and other reactants remaining after the polymerization process. However, if further purification is desired, the polymeric products may be subjected to a leaching process with water and ambient temperature and pressure.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

I claim:

1. A method for the preparation of gel-free copolymer of 2-hydroxyethyl methacrylate and 4-hydroxybutyl acrylate substantially in the absence of a chain transfer agent comprising:

introducing monomeric 2-hydroxyethyl methacrylate containing ethylene glycol dimethacrylate impurities in the range of about 0.05 to 0.1% by weight with monomeric 4-hydroxybutyl acrylate into a solution of water and alcohol; and copolymerizing the 2-hydroxyethyl methacrylate and 4-hydroxybutyl acrylate to form a polymerization mixture.

2. The method of claim 1, wherein the monomeric 2-hydroxyethyl methacrylate contains impurities in a total amount of no more than about 3% by weight of the monomer, and wherein the impurities are selected from the group consisting of ethylene glycol dimethacrylate, diethylene glycol monomethacrylate, methacylic acid and mixtures thereof.

3. The method of claim 1, further comprising adding a polyalkylene glycol to the polymerization mixture, and removing said alcohol and water to form a hydrophilic pressure sensitive adhesive.

4. The method of claim 3, wherein the polyalkylene glycol is selected from the group consisting of polyethylene glycol, polypropylene glycol, copolymers of ethylene glycol and propylene glycol and mixtures thereof.

5. A method for the preparation of gel-free copolymer of 2-hydroxyethyl methacrylate and 4-hydroxybutyl acrylate substantially in the absence of a chain transfer agent comprising:

introducing monomeric 2-hydroxyethyl methacrylate containing ethylene glycol dimethacrylate impurities in the range of about 0.05 to 0.1% by weight with monomeric 4-hydroxybutyl acrylate into an alcohol; and copolymerizing the 2-hydroxyethyl methacrylate and 4-hydroxybutyl acrylate to form a polymerization mixture.

6. The method of claim 5, wherein the monomeric 2-hydroxyethyl methacrylate contains impurities in a total amount of no more than about 3% by weight of the monomer, and wherein the impurities are selected from the group consisting of ethylene glycol dimethacrylate, diethylene glycol monomethacrylate, methacylic acid and mixtures thereof.

7. The method of claim 5, further comprising adding a polyalkylene glycol to the polymerization mixture and removing said alcohol to form a hydrophilic pressure sensitive adhesive.

8. The method of claim 7, wherein the polyalkylene glycol is selected from the group consisting of polyethylene glycol, polypropylene glycol, copolymers of ethylene glycol and propylene glycol and mixtures thereof.

9. The process of claim 1, wherein the copolymer is further purified by leaching.

10. The process of claim 5, wherein the copolymer is further purified by leaching.

* * * * *